United States Patent [19]

Schwartz

[11] Patent Number: 4,539,180
[45] Date of Patent: Sep. 3, 1985

[54] APPARATUS FOR QUANTITATIVELY DETERMINING THE LEVEL OF HEMOGLOBIN IN A BIOLOGICAL SAMPLE

[75] Inventor: Samuel Schwartz, St. Louis Park, Minn.

[73] Assignee: Regents of the University of Minnesota, Minneapolis, Minn.

[21] Appl. No.: 480,857

[22] Filed: Mar. 31, 1983

Related U.S. Application Data

[62] Division of Ser. No. 190,399, Sep. 24, 1980, Pat. No. 4,378,971.

[51] Int. Cl.³ .................... G01N 21/75; G01N 33/52; G01N 33/72
[52] U.S. Cl. ........................................ 422/58; 128/757; 422/61; 422/68; 422/99; 436/66; 436/172
[58] Field of Search ........... 73/864.51, 864.63, 864.64, 73/864.72; 128/638, 749, 754, 757, 759; 250/461.2; 356/40; 422/52, 58, 61, 68, 99, 102, 104; 436/63, 66, 172, 174, 179

[56] References Cited

U.S. PATENT DOCUMENTS

| | | | |
|---|---|---|---|
| 2,835,246 | 5/1958 | Boettger | 128/757 |
| 3,104,209 | 9/1963 | Scott | 436/95 X |
| 3,282,114 | 11/1966 | Pell | 73/864.72 |
| 3,290,117 | 12/1966 | Adams et al. | 422/56 |
| 3,400,708 | 9/1968 | Scheidt | 128/757 |
| 3,626,762 | 12/1971 | Gilford | 422/102 X |
| 3,713,985 | 1/1973 | Astle | 422/102 X |
| 3,939,044 | 2/1976 | Wilkins et al. | 128/759 X |
| 3,992,150 | 11/1976 | Retzer | 436/66 X |
| 4,027,658 | 6/1977 | Marshall | 128/757 |
| 4,260,392 | 4/1981 | Lee | 436/88 X |

FOREIGN PATENT DOCUMENTS 7302640 8/1974 Netherlands ................. 73/864.51

OTHER PUBLICATIONS

Morrison, Analytical Chemistry, vol. 37, pp. 1124–1126, (1965).
Grinstein, J. of Biol. Chem., vol. 167, pp. 515–519, (1947).
Wang et al., J. Sci. Food Agric., vol. 30, pp. 1089–1096, (1979).

Primary Examiner—Arnold Turk
Assistant Examiner—Robert J. Hill, Jr.
Attorney, Agent, or Firm—Dorsey & Whitney

[57] ABSTRACT

A method of quantitatively determining the level of hemoglobin in a biological material which includes the steps of preparing a test sample of the biological material, converting the heme portion of the hemoglobin in the test sample to porphyrin, assaying the fluorescence of the converted porphyrin and comparing the fluorescence of the converted porphyrin to a standard. The invention also relates to an apparatus for performing the above method and a sampler device for collecting and preparing a test sample of the biological material, wherein the apparatus includes at least two reaction chambers with one chamber containing oxalic acid and ferrous oxalate for converting the heme portion of hemoglobin in a test sample to porphyrin and the other chamber containing citric acid which is generally non-reactive with the heme portion of hemoglobin to function as a control blank for the hemoglobin determination.

2 Claims, 15 Drawing Figures

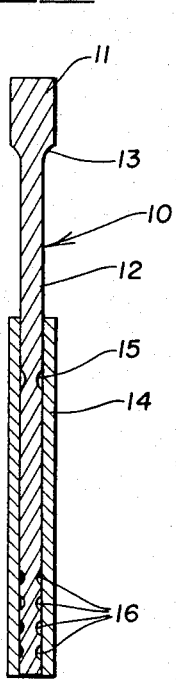
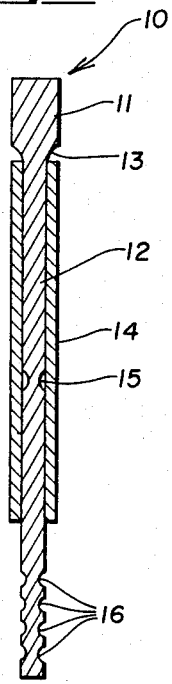
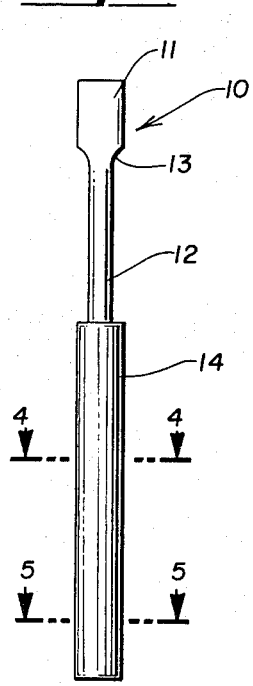
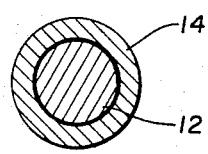
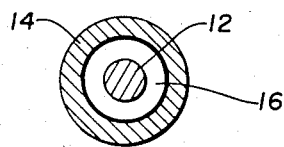
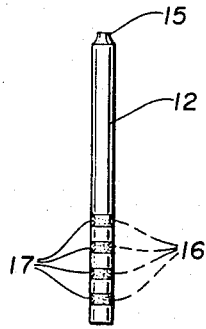

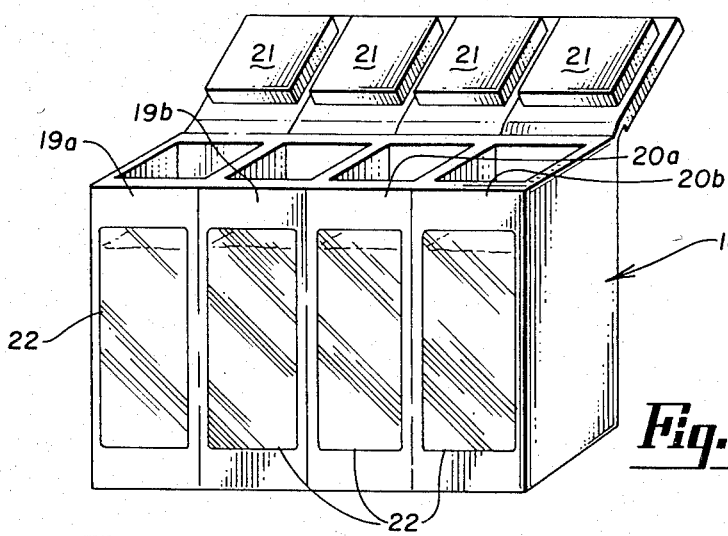
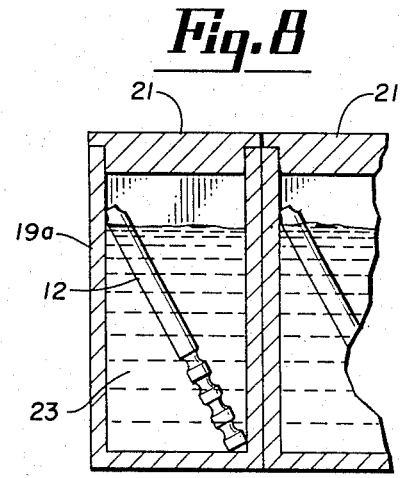
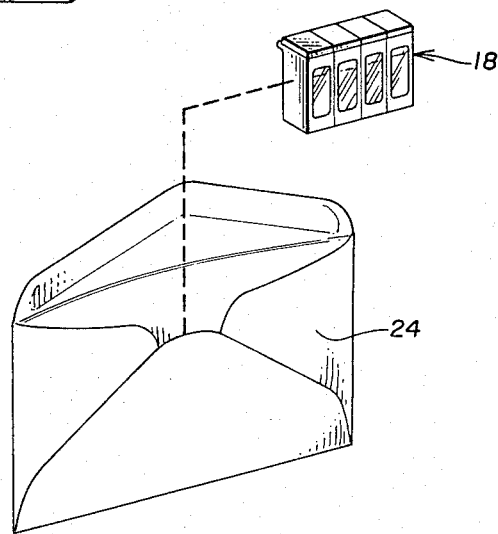
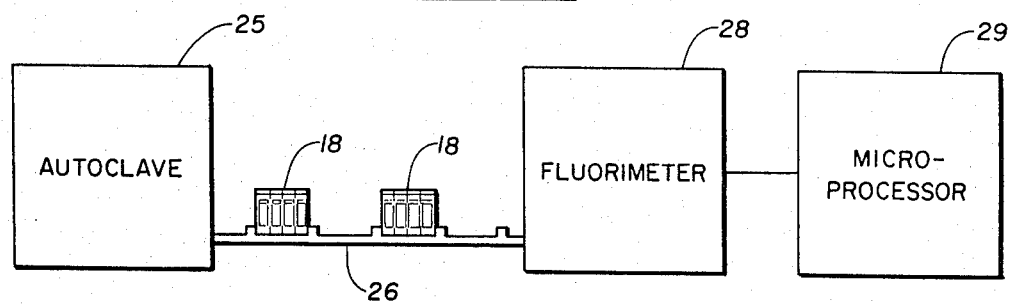

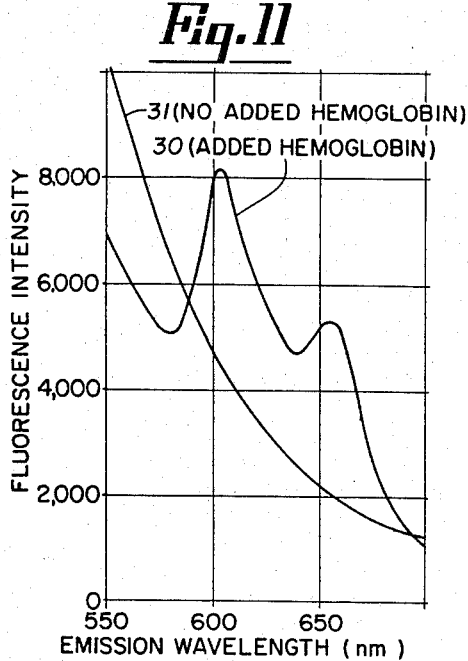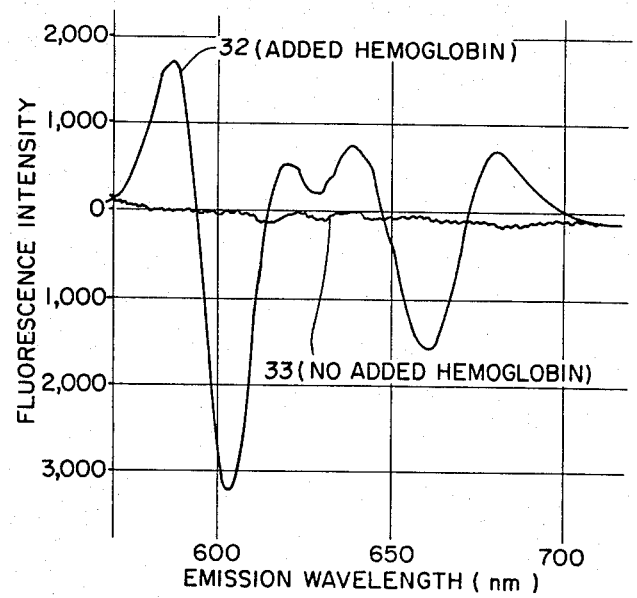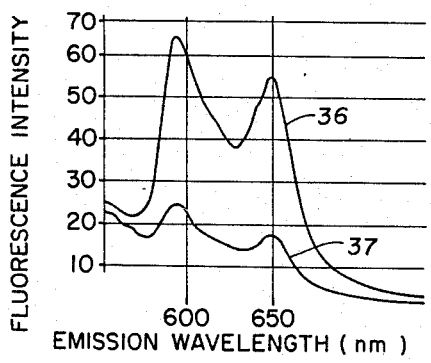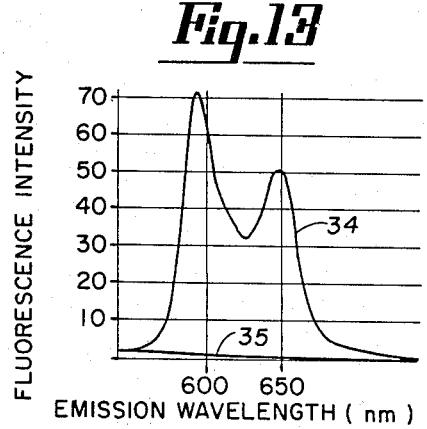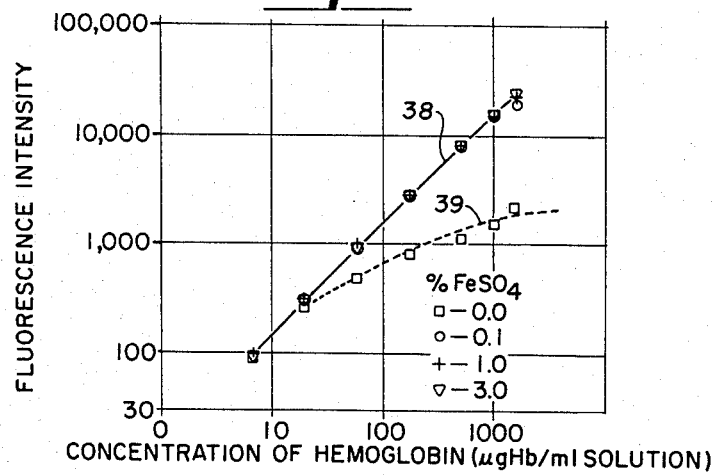

APPARATUS FOR QUANTITATIVELY DETERMINING THE LEVEL OF HEMOGLOBIN IN A BIOLOGICAL SAMPLE

The invention described herein was made in the course of work under a grant or award from the Department of Health, Education and Welfare.

This is a division, of application Ser. No. 190,399, filed 9/24/80, now U.S. Pat. No. 4,378,921.

BACKGROUND OF THE INVENTION

The present invention relates generally to a specific and quantitative test for hemoglobin including a method and apparatus for conducting such test and apparatus for collecting and preparing a sample for testing. More particularly, the invention relates to a test, and related method and apparatus, for quantitatively determining the level of hemoglobin in a biological material by converting the non-fluorescing heme portion of the hemoglobin to fluorescing porphyrin and assaying the fluorescence thereof. This test has particular applicability to a biological material such as feces or urine.

Various rapid screening tests for determining the presence of increased levels of hemoglobin in biological materials such as feces are currently available. These tests are used throughout the medical profession as the primary screening test for intestinal tumors. It is estimated that in excess of one million such tests are conducted each year in the United States for this purpose. Despite the fact that these tests do not yield quantitative data and that errors in test results are extremely costly, both personally and financially, and despite the fact that the tests currently available provide significantly high false positive and false negative results, their use is continued because there is no alternative.

The screening tests for hemoglobin in feces currently available do not involve converting the heme portion of hemoglobin to porphyrin and assaying its fluorescence; rather, currently available tests are indirect tests based on the peroxidase-like (pseudoperoxidase) activity of the hemoglobin. In these tests, colorless leuco dyes, in the presence of hemoglobin, become colored following addition of a suitable peroxide. Such tests, however, have several limitations. First, because of various factors including non-specificity and the fact that the reactivity is generally interfered with or affected by materials such as iron, ascorbic acid, or alterations in the hemoglobin molecule, significantly high false positive and false negative results are common. Secondly, interpretation of commercially available tests is often confusing because test results are reported only as being "positive" or "negative". In addition to inherent differences in sensitivity of the different tests, the amount of feces included in test samples may easily vary by factors of 20 or more. These factors, as well as the above-noted non-specificities and differences in personal interpretation of color development, all contribute to limiting the usefulness of these tests. Because of these limitations, occult blood assay is among the few remaining non-quantitative tests in clinical and laboratory medicine.

Although no quantitative tests for hemoglobin in feces or urine involving the conversion of heme to protoporphyrin are currently available in the prior art, various studies have previously been done regarding this conversion. For example, in a study by G. R. Morrison in a paper entitled *Fluorometric Microdetermination of Heme Protein*, (Anal. Chem., 37:1124–1126, 1965) a method for measuring heme protein in animal tissues involving the conversion of heme to porphyrin through the use of oxalic acid with a subsequent assay for fluorescence was described. This method, however, was ineffective for quantitatively determining hemoglobin levels in excess of certain concentrations. Under the conditions described by Morrison, feces having elevated levels of hemoglobin would have to be diluted several thousand-fold. Such extreme dilution is not suitable for large-scale screening tests.

Accordingly, there is a need in the art for a quantitative test, including the method and apparatus for conducting such test and the apparatus for collecting and preparing the test sample, for determining the level of hemoglobin in biological materials such as feces or urine which eliminates or substantially reduces the incidence of false positives and false negatives and which is readily suitable for mass screening purposes.

SUMMARY OF THE INVENTION

In contrast to the prior art, the method and apparatus of the present invention eliminates false positive and false negative results and has particular suitability for mass screening applications. The essential principles underlying the present invention have been developed for use in a laboratory procedure as well as in an automated commercial procedure. Apparatus has also been developed for collecting and preparing an appropriate fecal test sample for use in either laboratory or automated procedure. The test to which the present invention relates has been shown to be (1) specific for heme compounds such as hemoglobin including the total proto-heme content of the biological samples, (2) free of interference from other materials in the sample, particularly those present in feces, gastric juice, or urine, (3) extremely sensitive, (4) applicable for quantitative assay over a range of hemoglobin concentrations differing by a factor of more than 75,000, from concentrations of less than 0.02 micrograms per ml to more than 1,500 micrograms per ml of test solution, and (5) unaffected by compounds such as iron, ascorbic acid, hydrochloric acid, aspirin or alcohol which are known to affect some leuco-dye tests.

According to the specific procedure of the present invention, non-fluorescing hemoglobin is converted quantitatively to fluorescing porphyrin at all concentrations of hemoglobin tested. This conversion takes place when heme compounds in the sample are heated in the presence of appropriate concentrations of a converting reaction mixture of a reducing acid such as oxalic acid and a reducing salt such as ferrous oxalate. In this procedure, the concentration of porphyrin formed is determined by fluorescence assay. Such fluorescence assay is carried out on the reaction product in a solid system or following suitable extraction or dilution of the reaction product in a liquid system.

Since most biological samples, including feces and urine samples, have fluorescence which is not related to the heme compound reaction, the amount of such "nonspecific" fluorescence (including that from porphyrins which are excreted normally) is assayed in a separate sample in which citric acid or a similarly suitable nonreacting composition is substituted for the oxalic acid:ferrous oxalate system. Citric acid does not convert significant amounts of heme to porphyrin as the oxalic acid:ferrous oxalate system, but does produce the similar acid conditions required for analysis of the portion of fluorescence which is not related to heme content.

Subtraction of the fluorescence value found in the citric acid "blank" from that found in the oxalic acid:ferrous oxalate sample yields a value for fluorescence which is due specifically to the protoporphyrin formed from heme in the oxalic acid:ferrous oxalate sample. From this fluorescence difference, compared with a standard of known levels of hemoglobin (or protoporphyrin) concentration, the concentration of heme compounds or hemoglobin in the feces, urine, or other biological material sample tested can be calculated.

An automated rapid screening method based on similar principles is also provided for the quantitative assay of fluorescence in a solid system. This latter simplified system includes special features to overcome the loss ("quenching") of fluorescence due to excessive absorption of near-ultraviolet light (the wavelength at which porphyrin is caused to fluoresce most intensely) which results from high concentrations of hemoglobin and other pigments. The automated procedure also contemplates the reaction mixture having a gel or paste-like consistency at room temperature, but which liquifies when heated.

The present invention also includes an improved apparatus for collecting and preparing a known quantity of test sample of the biological material to be tested. Such apparatus has particular use in collecting and preparing a fecal sample and determining the level of hemoglobin in such sample. In general, this apparatus includes a sample collecting device and a plurality of reaction chambers, each containing an appropriate quantity of either the reaction mixture or the non-reactive composition. The sampler device is constructed of materials which are solid at ambient temperatures, but which liquify and become mixed with the material in the various reaction chambers when exposed to temperatures at which the conversion reaction is carried out. In the preferred embodiment, the composition of the sampler device is similar to that of the materials which are used as vehicles for the oxalic acid:ferrous oxalate and the citric acid samples.

Accordingly, an object of the present invention is to provide an improved test for specifically and quantitatively determining the level of hemoglobin in a biological material.

A further object of the present invention is to provide an improved method and apparatus for specifically and quantitatively determining the level of hemoglobin in a test sample by converting the heme portion of the hemoglobin to porphyrin and assaying the fluorescence thereof.

A further object of the present invention is to provide an improved method and apparatus for specifically and quantitatively determining the level of hemoglobin in a biological test sample, which test has particular suitability for mass screening.

A further object of the present invention is to provide an improved method and apparatus for specifically and quantitatively determining the level of hemoglobin in a test sample of a biological material such as feces or urine over a range of hemoglobin concentrations sufficient to cover all possible hemoglobin concentrations therein.

Another object of the present invention is to provide an automated procedure for quantitatively determining the level of hemoglobin in a biological test sample in which the problem of excessive "quenching" during the fluorescence assay is overcome.

A further object of the present invention is to provide an improved method and apparatus for collecting and preparing a known quantity of a biological test sample for use in the test of the present invention.

These and other objects of the present invention will become apparent with reference to the drawings, the description of the preferred method and apparatus and the appended claims.

DESCRIPTION OF THE DRAWINGS

FIG. 1 is a cross sectional view of the sampler for collecting a fecal sample.

FIG. 2 is a cross sectional view of the sampler for collecting a fecal sample in which the sheath is in its upper position.

FIG. 3 is a plan view of the sampler for collecting a fecal sample.

FIG. 4 is a cross sectional view of the sampler for collecting a fecal sample as viewed along the section line 4—4 of FIG. 3.

FIG. 5 is a cross sectional view of the sampler for collecting a fecal sample as viewed along the section line 5—5 of FIG. 3.

FIG. 6 is a plan view of the lower end of the sample collection device showing the collected sample embedded in the grooves.

FIG. 7 is a pictorial view of the device or reaction kit in which the test reaction is carried out.

FIG. 8 is a view showing the inside of one of the reaction chambers with the reaction mixture and the test sample disposed therein.

FIG. 9 is a pictorial view showing the test sample reaction kit and the envelope in which the same is mailed.

FIG. 10 is a schematic view showing the automatic processing equipment of the present invention.

FIG. 11 is a graph showing the fluorescence spectra of a gel reaction mixture (oxalic acid:ferrous oxalate), with and without added hemoglobin.

FIG. 12 is a graph showing the second derivative of the fluorescence spectra shown in FIG. 11.

FIG. 13 is a graph comparing the fluorescence spectra of hemoglobin in an oxalic acid:ferrous oxalate solution with that of hemoglobin in a citric acid blank. Fluorescence levels are plotted on the vertical axis and emission wavelengths are plotted on the horizontal axis.

FIG. 14 is a graph comparing the fluorescence spectra of a test sample of feces in an oxalic acid:ferrous oxalate solution with that of a test sample from the same fecal sample in a citric acid blank. Fluorescence levels are plotted on the vertical axis and emission wavelengths are plotted on the horizontal axis.

FIG. 15 is a graph showing linearity between hemoglobin and fluorescence in an oxalic acid:ferrous oxalate solution with iron added as ferrous sulfate. Concentration of hemoglobin is plotted on the horizontal axis and fluorescence levels are plotted on the vertical axis.

DESCRIPTION OF THE PREFERRED METHOD AND APPARATUS

The quantitative test of the present invention includes three basic method steps. The first includes preparing a test sample of the biological material of which the level of hemoglobin is to be quantitatively tested; the second includes quantitatively converting the non-fluorescing heme portion of the hemoglobin in the test sample to fluorescing porphyrin; the third includes assaying the fluorescence of the porphyrin as well as a blank sample and comparing the difference in fluorescence to the fluorescence of a control standard of known hemoglobin concentration. In the development of the present invention, both a laboratory procedure utilizing the fluorescence assay of a liquid system and an automated procedure utilizing the fluorescence assay of a solid system have been developed. While many of the procedural details of the laboratory and automated tests differ, the basic principles are the same. An improved device or kit for collecting and preparing the test sample in the automated procedure has also been developed. A known amount of feces can be obtained with the fecal sampler of this kit for either the laboratory or the automated method. Each of the above features of the present invention will be discussed in detail below.

In the laboratory procedure, the preparation of the test sample includes the first step of collecting, mixing and determining the weight or volume of a test sample of the biological material of which the hemoglobin level is to be determined. While it is contemplated that the methods and apparatus of the present invention have applicability to many different biological materials, it has particular applicability to fecal and urinary samples; thus the description of the preferred method and apparatus will be with reference to a fecal sample. A test quantity of the fecal sample is first collected and weighed (i.e.) 0.5 gram. This test sample is then added to approximately 20-40 volumes of a salt solution containing approximately 0.85 percent sodium chloride and homogenized to yield a uniform dispersion of the feces. The purpose of combining the test sample with the salt solution is to dilute the feces, including its hemoglobin and other pigments, and to provide increased stability. It is known that low concentrations of hemoglobin are more stable in a salt solution than in water. A fecal homogenate having approximately a 2.5% to 5% test sample concentration has been found to be preferable, though not critical. The test sample prepared in the above manner can be stored in a frozen state at $-15°$ C. to $-30°$ C. until ready for use.

When the test is ready to be performed, the prepared test sample is mixed with a quantity of a reducing acid and a reducing salt. On heating, the heme portion of the hemoglobin is converted to porphyrin. While it is contemplated that other reducing acids and salts might be acceptable, the reducing acid is preferably oxalic acid and the reducing salt is preferably ferrous oxalate or ferrous sulfate. During the above conversion reaction, iron is removed from the non-fluorescing heme molecule, resulting in the iron-free fluorescing protoporphyrin which fluoresces red on exposure to near ultraviolet light at the approximate wave length of 408 nanometers (nm). It also fluoresces, though less intensely, when exposed to green light at the approximate wavelength of 558 nm, or to yellow light at the approximate wavelength of 600 nm. Trace amounts of other similar fluorescing porphyrins may also be formed.

In the preferred system, 2 molar oxalic acid and sufficient ferrous oxalate or ferrous sulfate is mixed to yield a 1% solution. Use of either ferrous salt results in a linear relationship between assayable fluorescence and hemoglobin concentrations up to the highest concentration tested, namely 1,620 micrograms of hemoglobing per ml of reacted solution (about 50 micrograms of heme per ml). Use of ferrous sulfate, however, leads to increased acidity because it forms sulfuric acid, as well as ferrous oxalate, when added to oxalic acid. Further, the ferrous sulfate has been added as a 20% aqueous solution which must be made up fresh within a few hours of use because it undergoes oxidation to the ferric salt. Use of ferrous oxalate also results in good linearity providing it is substantially pure (99%). Impurities in the ferrous oxalate tend to adversely affect the linearity of the reaction at low concentrations of hemoglobin. While both ferrous sulfate and ferrous oxalate, as well as other ferrous salts can be used, ferrous oxalate is preferred.

To produce a 1% solution of ferrous oxalate, 1 gram of ferrous oxalate is added to 99 milliliters of 2 molar oxalic acid. The test sample homogenate is then added to a quantity of this solution and heated at 120° C. for 90 minutes. The speed and completeness of the reaction (the conversion of heme to porphyrin) will vary with the temperature; thus, while temperatures in the range of 60° C. to 100° C. will convert heme to porphyrin in this mixture, the reaction will occur quite slowly. In general, the temperature and the dwell time within the autoclave should be sufficient to convert all the heme to porphyrin. While the preferred procedure contemplates combining 20 microliters of the test sample homogenate with 1,000 microliters of the oxalic acid:ferrous oxalate solution, various other quantities of test sample homogenate, such as quantities between 5 microliters and 100 microliters have been found to be acceptable. The oxalic acid:ferrous oxalate solution can be prepared in advance and stored at $-30°$ C.

The function of the reducing salt, which in the preferred procedure is ferrous oxalate, is important in that its presence provides a marked increase in the linear range of assayable hemoglobin. Thus, with the present procedure, quantitative recovery of fluorescent porphyrin over a wider range of concentrations is possible. To remove the iron from hemoglobin and thus convert the heme molecule to protoporphyrin, three elements are necessary: (1) reducing conditions, (2) a strong acidic environment, and (3) heat. The reducing acid and in particular oxalic acid provides reducing conditions and an acidic environment. By itself it will remove heme from the protein portion of hemoglobin, and then remove iron from heme to convert it to porphyrin. However, it has been found that oxalic acid alone is effective in this conversion reaction only for relatively low concentrations of hemoglobin, on the order of up to 15 micrograms per milliliter of oxalic acid solution. Because the hemoglobin level in many biological samples, particularly fecal samples, can be many times greater than that, oxalic acid or any other reducing acid alone is generally ineffective and of little use at such high concentrations of hemoglobin unless the hemoglobin is diluted many hundred or thousand-fold. For quantitative determination of higher concentrations of hemoglobin, the ferrous oxalate or ferrous sulfate acts as an additional reducing agent to increase the reducing conditions, thus increasing the conversion and insuring that all of the heme in the hemoglobin of the test sample has been converted to porphyrin. This results in a straight line fluorescence curve as illustrated in FIG. 15 over a concentration range sufficient for all possible levels of hemoglobin in the biological sample, under the conditions recommended.

In FIG. 15, concentration of autoclaved hemoglobin is plotted against fluorescence intensity for concentrations of added ferrous sulfate of 0.0%, 0.1%, 1.0% and 3.0%. As shown, the curve 39 generated with no ferrous sulfate becomes non linear at higher concentrations of hemoglobin. The curve 38, however, generated by the 0.1%, 1.0% and 3.0% concentrations of ferrous sulfate are linear. This linearity enables the concentration of hemoglobin to be determined by measuring the fluorescence intensity and comparing the same to a standard. In FIG. 15, the exciting wavelength is 410 nm while the emission wavelength is 660 nm. These autoclaved samples were diluted until colorless prior to fluorescence assay.

In the preferred laboratory procedure, it has been found that an oxalic acid solution containing approximately 0.1% to 5.0% ferrous oxalate converts all of the heme to protoporphyrin over the range of hemoglobin concentrations found in the biological test samples with which the present test is intended to be used. A concentration of 1.0% ferrous oxalate is preferred.

Following conversion of the heme to protoporphyrin, the oxalic acid and test sample mixture is allowed to cool. Its fluorescence is then assayed. To prepare the mixture for this assay, two procedures are available. First, the mixture can be centrifuged with the supernatent solution being removed, diluted with 0.5 molar oxalic acid and its fluorescence assayed. In this procedure, the precipitate consists of iron oxalate and insoluble fecal residue, while the supernatant solution contains all of the porphyrin formed from heme plus a small amount of fecal pigments, native porphyrins and some iron oxalate.

In a second, preferred, procedure for preparing the oxalic acid and test sample mixture for the fluorescence assay, approximately 100 microliters of the mixture, approximately 1200 microliters of an ethyl acetate:glacial acidic acid solution in a 4:1 ratio, and approxiamtely 400 microliters of 3 molar sodium acetate are mixed and shaken together and then centrifuged. The supernatent solution is then assayed for fluorescence. Use of the procedure involving addition of the ethyl acetate:glacial acidic acid solution and sodium acetate is preferable since it results in a purified and essentially colorless solution, therefore allowing for a more specific and accurate fluorescence assay. In this system the sodium acetate functions to partially neutralize the oxalic acid, thus converting a portion of it to sodium oxalate. Most of the sodium and iron oxalates remain with the precipitate left behind following centrifugation. The fluorescence can be assayed with any conventional and reasonably sensitive fluorimeter or spectrofluorophotometer. In the preferred procedure, results have been obtained with spectrofluorophotometers manufactured by Aminco Bowman or by Perkin Elmer. Special types of spectra such as second derivatives, synchronous scans, etc. have been recorded with the Perkin Elmer model MPF-44B.

Because of the presence of a certain amount of naturally occurring fluorescing materials, including naturally occurring protoporphyrin and other porphyrins in all biological test samples, existence of this native fluorescence must be accounted for. To do this, a blank control of a duplicate test sample is prepared and similarly assayed for fluorescence. In this blank control however, 1.5 molar citric acid is substituted for the oxalic acid and ferrous oxalate. Otherwise the procedure is identical. It has been found that the use of citric acid does not convert any significant amount (less than 0.2%) of the heme to porphyrin. Thus when this blank control solution is prepared and assayed for fluorescence, its fluorescence intensity will reflect almost entirely the fluorescence of porphyrins and other materials naturally occurring in the test sample. The actual quantitative determination of hemoglobin in the test sample is then determined by comparing the difference between the fluorescence intensity of the reaction sample and blank control to a control standard prepared with known concentrations of hemoglobin.

In the fluorescence assay, the test sample is exposed to an excitation light source and the emitted fluorescence from the test sample is measured. In the preferred procedure (extraction into ethyl acetate) fluorescence is most sensitive when excited at about 401 nm. Three weaker excitation peaks are found between approximately 500 and 580 nm, and may have some advantages under special conditions. With each of these fluorescing peaks, the fluorescing porphyrins from fecal samples show a sharp fluorescence peak at about 630 nm. During a fluorescence assay the fluorescence levels at this wavelength for ethyl acetate extracts of both the test sample in which heme has been converted to fluorescing porphyrin and the citric acid are compared. The difference between them is then compared to a standard and the hemoglobin concentration determined. If the autoclaved solutions are diluted with oxalic acid, the excitation wavelength is set at 410 nm, and fluorescence is assayed at 660 nm. Fluorescence in acid solution may also be assayed at about 610 nm, but specificity is reduced at the latter wavelength.

FIGS. 13 and 14 show fluorescence spectra of both a citric acid mixture and an oxalic acid:ferrous oxalate mixture. FIG. 13 shows a fluorescence spectrum 34 of added hemoglobin in an oxalic acid:ferrous oxalate system and a fluorescence spectrum 35 of added hemoglobin in a citric acid system. Thus, spectrum 34 reflects the hemoglobin converted to porphyrin. Spectrum 35 confirms that the citric acid system converts no significant amount of hemoglobin to porphyrin.

FIG. 14 shows a fluorescence spectrum 36 of a fecal specimen with ingested hemoglobin in an oxalic acid:ferrous oxalate system and a fluorescence spectrum 37 of the same fecal specimen with ingested hemoglobin in a citric acid blank system. The spectrum 36 reflects the fluorescence of porphyrin derived from heme by the oxalic acid:ferrous oxalate as well as native porphyrins. The spectrum 37 reflects only fluorescence of native porphyrins plus some non-porphyrin fluorescence. Thus, the difference in fluorescence between the spectra 36 and 37 for a specific wavelength reflects converted porphyrin, which in accordance with the present invention, is linearly related to the heme or hemoglobin in the sample. The actual quantitative value of hemoglobin can be determined by comparing this fluorescence to a standard.

An example of the above discussed laboratory procedure is as follows. First, a 2.5% fecal homogenate in a saline solution is prepared. Next, 100 grams of a reaction mixture is prepared by combining 25.2 grams of oxalic acid, 1.0 gram of powdered ferrous sulfate or ferrous oxalate and 73.8 milliliters of water. These ingredients are heated in a boiling water bath to dissolve and mix the same. Most of the ferrous oxalate remains insoluble. The reaction mixture is then divided among several tubes or vials which are sealed and kept at −30° C. until ready for use. 100 grams of a control blank mixture is also prepared by combining 28.8 grams of citric acid and 71.2 milliliters of water. Next, 50 microliters of the 2.5% fecal homogenate are added to each of several tubes in which the assay is to be conducted. 1.0 milliliter of either the warmed oxalic acid:ferrous oxalate mixture or the blank mixture is added to each tube. These tubes are then mixed well on the vortex, covered with Saran wrap with holes punched in the top. The tubes are then heated in an autoclave for 90 minutes at 120° C. and then allowed to cool to room temperature. Cooling may be hastened by placing in a cool water bath. Extraction into ethyl acetate or centrifugation and dilution with 0.5 molar oxalic acid are then performed as earlier described.

Since protoporphyrin comprises about 3.37% of the hemoglobin molecular weight, the porphyrin values are multiplied by 100/3.37, or 29.67, to derive the corresponding amount of hemoglobin. Milligrams of hemoglobin per gram of feces values are then determined by multiplying by appropriate dilution factors.

The automated procedure utilizing the method of the present invention employs the same general principles as described above. However, certain details are modified to facilitate large scale screening application of the method. Similar to the laboratory procedure, the automated procedure requires the collection of a test sample of the biological material to be tested. As with discussion of the laboratory procedure, the automated procedure will be described with reference to a fecal sample as the biological material. In the preferred method, the test sample is collected with the sampler device illustrated in FIGS. 1–5. With reference to these figures, it can be seen that this device indicated generally by the reference numeral 10 includes an elongated generally cylindrical sampler rod 12 and an upper generally cylindrical portion 11 with a diameter greater than the rod 12. The rod portion 12 is integrally formed with the section 11 at the shoulder 13. The sampler rod portion 12 includes a breakage point 15 which allows the rod 12 to be broken into two pieces after the test sample has been collected. The lower end of the rod 12 includes a plurality of grooves 16 extending about the periphery of the rod 12 for collection of the test sample.

The device 10 also includes a generally cylindrical tubular member or sheath 14 having an internal diameter approximating the exterior diameter of the rod section 12, thus permitting the sheath 14 to slide over the rod 12 with little tolerance therebetween. This particular sampler rod 12 is adapted for collecting a predetermined amount of a fecal sample. To operate the sampler device 10, the sheath 14 is raised so that its upper edge engages the shoulder portion 13 as illustrated in FIG. 2. The lower end of the rod 12 is then lowered through the feces to a point just below the lower level of the sheath 14. During this insertion of the rod 12, the rod is rotated one or two turns to insure that a sufficient sample of the fecal material becomes embedded in the grooves 16. The rod 12 is then removed from the feces and the sheath 14 is lowered through the entire rod section 12. Because of the small tolerance between the exterior diameter of the rod 12 and the interior diameter of the sheath 14, substantially all of the feces from the rod 12 is removed, except that which remains in the grooves 16.

After the sheath 14 has been removed, it is discarded and the rod 12 is broken at the break point 15. The lower end of the rod 12 as illustrated in FIG. 6 is then placed into a reaction chamber in a structure such as that illustrated in FIGS. 7 and 8. As illustrated, FIG. 7 shows a structure 18 having a plurality of reaction chambers 19a, 19b, 20a and 20b. These reaction chambers are provided with a cap or cover 21 which is hinged to the main body. Each of the reaction chambers is also provided with a transparent window 22 which is sufficiently transparent to light at wavelengths from about 350 to 700 nm. This enables the fluorescence of the material within the chamber to be assayed directly through the windows 22.

As will be described in detail below, each of the chambers 19a, 19b, 20a and 20b is partially filled with a reaction mixture of a reducing acid and reducing salt such as an oxalic acid:ferrous oxalate reaction mixture or a blank mixture such as a citric acid control. In the preferred embodiment, the chambers 19a and 20a are provided with the reaction mixture such as the oxalic acid and ferrous oxalate composition, while the chambers 19b and 20b are provided with the control mixture such as the citric acid composition. The mixtures in the reaction chambers are intended for combination with the test sample. The device 18 containing the reaction chambers can be constructed of many different materials, but preferably should be constructed from any of several available plastics having the following properties. First, the reaction chambers, or at least the windows 22, should be sufficiently transparent to light from about 350 nm to 700 nm to facilitate the fluorescence assay. Second, the material should not react with the reaction chamber contents or interfere significantly in any other way with the assay. Thirdly, the material must maintain optical and chemical stability when heated at 120° C. in an autoclave or in an oven.

The next step in the method of the present invention is to convert the heme portion of the hemoglobin in the test sample to metal-free porphyrin. As described above in connection with the laboratory procedure, this was done by addition to the appropriate mixture of the sampler device or of a measured volume of homogenized, diluted material being tested. In the preferred method of the automated procedure, the prepared test samples are combined with a reducing acid and a reducing salt, namely oxalic acid and ferrous oxalate, within the reaction chambers 19a and 20a. Each of these chambers 19a and 20a contains a combination of 2 molar oxalic acid and 1/18 (0.05) molar ferrous oxalate together with a suitable vehicle material. Concentrations of about 0.01 to 0.2 molar ferrous oxalate yield satisfactory results. Preferably the vehicle comprises a mixture of polyethylene glycols of different molecular weights. Although the vehicle may be of different consistencies or properties, (i.e.) solids or powders such as fiber glass, celulose powders and metal salts impregnated with the oxalic acid or citric acid, liquids, etc., the vehicle preferably has a gel, paste-like or non-flowing consistency at room temperatures to prevent it from spilling or leaking or flowing from the reaction chambers in the kit 18. Preferably, the vehicle liquifies at temperatures greater then about 100° C. The amount of reaction material supplied to each of the chambers 19a and 20a is sufficient to react with the quantity of fecal specimen collected with the sampler device described above.

The reaction chambers 19b and 20b in the device or reaction kit 18 illustrated FIG. 7 are provided with a similar vehicle material, but with a non-reducing acid in place of the oxalic acid:ferrous oxalate mixture. In the preferred method, this non-reducing acid is 1.5 molar citric acid. Thus, the chambers 19b and 20b are control blank chambers which are used to assay only the naturally occurring fluorescence in the test sample.

In the preferred embodiment, each of the chambers 19a, 19b, 20a and 20b is filled to about 50–60 percent of capacity with either the oxalic acid:ferrous oxalate system or the citric acid system. When the sampler rod 12 (FIG. 6) together with the collected test sample is added, the chamber is filled to about 65-75 percent capacity as illustrated in FIG. 8.

The total number of chambers in each device may be varied; however, each device is preferably provided with corresponding pairs of chambers for the collection of duplicate samples. One of the samples is to be used in the reaction chamber in which heme is converted to porphyrin, while the other is to be used in the control blank chamber. Thus, in the device illustrated in FIG. 7 having a total of four chambers, four samples of a single bowel movement or two samples from each of two bowel movements is possible. It is contemplated that these samples could be collected by the patient utilizing the device shown in FIGS. 1-6 and that the same could then be mailed in a suitable envelope 24 (FIG. 9) to a central laboratory for processing and analysis.

It is contemplated that the vehicle containing the reaction mixture of a reducing acid and a reducing salt and the blank mixture of an inert acid can comprise many different compositions. Although the procedure can be run in a liquid, solid or various other types of systems, the vehicle preferably has a gel, paste-like or non-flowing consistency at room temperatures and liquifies at temperatures above approximately 100° C. The vehicle composition should also have a low or negligible fluorescence to avoid interference with the fluorescence assay of the test and should be stable under all conditions of the reaction. The use of a semi-solid gel-like vehicle has special advantages when used by relatively untrained individuals and when intended for shipment by mail. When these limitations do not apply, it may be advantageous to add the feces and fecal sampler directly to aqueous solutions of oxalic acid:ferrous oxalate and of citric acid, since these aqueous solutions exhibit less non-specific (blank) fluorescence than do those which contain gel-forming agents. In the preferred embodiment the vehicle comprises a mixture of polyethylene glycols and similar high molecular weight compounds such as poly(ethylene oxides). A reaction mixture which has been found to be acceptable includes a mixture of 73.8 grams of polyethylene glycols, 25.2 grams of oxalic acid and 1.0 gram of powdered ferrous oxalate. If ferrous sulfate is used, 1.0 gram of ferrous sulfate is substituted for the ferrous oxalate. A control blank mixture which has been found to be acceptable includes a mixture of 71.2 grams of polyethylene glycols and 28.8 grams of citric acid. The above mixtures yield final concentrations of 2 molar oxalid acid and 1.5 molar citric acid, respectively.

The next step in the automated procedure is to heat the reaction chambers with the test samples and the reaction or non-reactioq materials disposed therein. Upon heating to the preferred temperature of 120° C., the sampler rod 12 containing the feces sample liquifies, thus liberating the collected feces into the reaction mixture. Heating to the 120° C. temperature also liquifies or solubilizes the reaction mixture, including the preferred polyethylene glycol vehicle and either the oxalic acid:ferrous oxalate reactants or the citric acid material. In the chambers 19a and 20a, the oxalic acid and ferrous oxalate react with the hemoglobin in the feces sample to convert the heme portion to fluorescing porphyrin. In the chambers 19b and 20b, no quantitatively significant reaction occurs. Although it is contemplated that the heating could occur at various temperatures and for various periods of time, the preferred automated method contemplates heating in a suitable autoclave or oven to the temperature of 120° C. for a period of 90 minutes. The temperature must be sufficiently high to liquify the reaction mixtures and to liquify the material from which the collection rod 12 is made. During the heating step, the reaction mixtures together with the feces sample, the liquified sampler rod and the vehicle are uniformly mixed. Following the heating step, this uniform mixture is cooled and resolidified.

In view of the above procedure in which the sampler rod 12 liquifies and uniformly mixes with the reacting materials, such rod 12 should have certain characteristics and features. For example, it should be solid and rigid at temperatures up to at least 50° C. and liquid at temperatures above 100° C. Further, it should remain completely mixed with the reacting materials on cooling and it should be stable such that heating or prolonged storage under normal ambient temperatures will not result in any significant change in its chemical or physical properties. The sampler rod 12 should also be constructed of a material which dissolves slowly in water and is miscible with the chemical reaction mixture in the reaction chamber when both are liquified during the heating period. It is also preferable if the sampler rod 12 is made of chemical compounds similar to those in the reaction mixture, such as polyethylene glycols, although this is not essential. The sampler rod 12 must also be constructed of a material which does not interfere with the conversion of the heme components to porphyrin or with the subsequent fluorimetric analysis. With these requirements, it has been found that a sampler rod 12 constructed primarily of polyethylene glycol having a molecular weight of about 20,000 combined either with polyethylene oxide having a molecular weight of about 100,000 or with other polyethylene glycols to modify the hardness of the material as desired can be used. As described previously, the sheath 14 which is eventually discarded can also be constructed from the same material as the sampler rod 12. It is contemplated, however, that various other mixtures of other molecular weights of these or similar compounds will also be suitable compositions for construction of the sampler rod 12.

After the fecal sample and the various reaction mixtures in the chambers 19a, 19b, 20a and 20b have been heated and subsequently cooled and resolidified, each reaction chamber is assayed for fluorescence. The general procedure is then similar to the laboratory procedure except that in liquids the exciting light source is transmitted through the sample with the fluorescense assayed at right angles, while in the solid, the front surface is assayed for fluorescence. In the assay, the fluorescence of each control blank sample, reaction chambers 19b and 20b, is subtracted from its respective reaction sample, reaction chambers 19a and 20a. The resulting difference between these fluorescence levels is then compared to fluorescence intensity of a standard of known hemoglobin concentration and the concentration of hemoglobin in the test sample is calculated. While the above steps can be done manually, the preferred procedure contemplates that the assay for fluorescence together with the subtraction of the fluorescence intensity of the blank control sample from the fluorescence intensity of the reaction sample, the comparison of this difference to the standard and the calculation of the quantitative level of hemoglobin in the test sample will be done automatically by an appropriate computerized microprocessor.

Thus, after cooling, the device 18 is removed from the envelope 24 (FIG. 9) in which the test sample was mailed and heated and placed onto a moving platform or conveyor 26 or other suitable means for conveyance to the station 28 for performing the fluorescence assay. The fluorescence of the samples in each of the chambers 19a, 19b, 20a and 20b is determined by exposing the same to a suitable light source (filter or monochrometer) system, and a photo-detector system. The fluorescence intensity determined for each of the chambers is then fed directly to the computerized microprocessor 29 for analysis and calculation of the quantitative level of hemoglobin per unit volume in the test sample.

In the above procedure, certain special precautions are necessary for the direct fluorescence assay of the chamber contents. These precautions are necessary primarily because of the presence of variable losses ("quenching") of fluorescence intensity due to excessive absorption of the incident near-ultraviolet light (approximately 410 nm) generally used to excite porphyrin fluorescence. This light absorption may be due to excessively large amounts of porphyrin, bile pigments, food particles, etc. Thus, unless these certain precautions are taken, excessive quenching may occur, thus reducing the fluorescence intensity and thus giving a lower calculated quantitative level of hemoglobin than is actually present in the fecal sample.

One precaution that can be taken, if appropriate instrumentation is not available, is to liquify the reaction and blank chamber contents by heating. A measured aliquot is then removed and assayed fluorimetrically following dilution and/or extraction as described in the laboratory procedure above. In the liquid system, "quenching" is generally a problem that can be easily dealt with simply by further diluting the solution whose fluorescence is being assayed. This is preferably done in an automated system, but may be done manually. In the automated system, approximately 10 to 30 microliters of liquified solution is preferably added to 100 to 300 microliters of 0.5 M oxalic acid. This combination is then mixed and passed through a narrow microcell for fluorimetric analysis. Excitation of flourescence by visable light at porphyrin excitation maxima of approximately 555 nm or 590 to 600 nm is recommended, since the later wavelengths (especially 590 to 600 nm) exhibit relatively less non-specific absorption of light and, hence, produce negligible fluorescence "quenching" in such diluted samples. They also excite less non-specific fluorescence by constituents of feces, urine and vehicles used to produce semi-solid gels than does the usually recommended excitation by near-ultraviolet light.

Several other alternatives are consistent with the goal of automation. Chief among these is the assay of fluorescence directly in the autoclaved sample, with automatic correction for fluorescence "quenching" due to light absorption. This correction by the computer is based on a simultaneous determination of light absorbance and fluorescence using reflected (or transmitted) light and a separate phototube for the absorbance assay. The use of "second derivative" fluorescence spectra or addition of a non-reactive and non-fluorescing pigment whose light absorption greatly exceeds that of any amount of other materials present in the chambers has also been considered. Under the latter alternative, essentially constant fluorescence "quenching" will be observed even in the presence of variable (and now relatively negligible) amounts of fecal pigment.

The use of the second derivative of fluorescence spectra may have significant advantages. A fluorescence spectrum 30 of a typical hemoglobin reaction sample is illustrated in FIG. 11 together with the fluorescence spectrum 31 of the similar solid reaction mixture without added hemoglobin. In this fluorescence spectrum, fluorescence intensity is plotted from 550 nm to 700 nm, with excitation at 408 nm. As shown, the fluorescence intensity at a wavelength of 604 nm for the reaction sample 30 is approximately 8,200 as compared to a fluorescence intensity of 4,500 for the blank sample 31 at this same wavelength. Thus, the fluorescence intensity of the reaction sample is less than twice as much as the fluorescence intensity of the blank sample. With certain computer equipment, however, the second derivative of this fluorescence spectrum can be plotted which in effect eliminates the nonspecific blank fluorescence. FIG. 12 shows the second derivative of the fluorescence spectra of FIG. 11. Specifically, the curve 32 represents the second derivative of the spectrum 30 and the curve 33 represents the second derivative of the spectrum 31. In this second derivative of fluorescence spectra, fluorescence intensity is measured as the difference between readings at wavelengths of successive minima and maxima of the respective curves 32 and 33. For the hemoglobin sample curve 32, this difference is approximately 4,900, the difference in the level between the positive reading at 587 nm and the negative reading at 604 nm, for example. For the blank (vehicle) sample, this difference is essentially zero. This significantly improves the accuracy and sensitivity of the test.

Although the description of the preferred embodiment has been quite specific, it is contemplated that various changes and modifications could be made to the method and apparatus of the present invention without deviating from the spirit thereof. Accordingly, it is contemplated that the scope of the present invention be dictated by the appended claims, rather than by the description of the preferred embodiment.

I claim:

1. An apparatus for quantitatively determining the level of hemoglobin in a biological specimen comprising:

a device for preparing first and second test samples of a biological specimen including means defining first and second reaction chambers, said first reaction chamber containing a first reaction mixture comprising oxalic acid and ferrous oxalate for converting the heme portion of hemoglobin in a first test sample to porphyrin and said second reaction chamber containing a second reaction mixture comprising citric acid which is generally non-reactive with the heme portion of hemoglobin in a second test sample;

means for heating first and second test samples in respective first and second reaction chambers in the presence of the respective first and second reaction mixtures to a temperature and for a duration to convert the heme portion of hemoglobin in said first test sample to porphyrin; and means for determining any fluorescence of porphyrin in said first and second test samples.

2. A test sample collection and preparation kit for use in connection with a test for quantitatively determining the level of hemoglobin in feces, said kit comprising:

sampler means for collecting a test sample of feces including an elongated sampler section having a plurality of peripheral grooves for collection of said test sample, said sampler constructed of a composition containing polyethylene glycol and being rigid at room temperatures and becoming a liquid upon heating to a temperature in excess of 100° C.;
a structure having a plurality of reaction chambers;
a first reaction mixture in at least one of said reaction chambers, said first reaction mixture comprising oxalic acid and ferrous oxalate and being effective to convert the heme portion of hemoglobin in a first test sample to porphyrin; and
a second reaction mixture in at least a second of said reaction chambers, said second reaction mixture comprising citric acid.

* * * * *